United States Patent [19]

Van Auken

[11] 4,350,832
[45] Sep. 21, 1982

[54] SYNTHESIS OF N-T-BUTYL-P-MENTHANE-3-CARBOXAMIDE

[75] Inventor: Thomas V. Van Auken, Richmond, Va.

[73] Assignee: Philip Morris, Incorporated, New York, N.Y.

[21] Appl. No.: 258,207

[22] Filed: Apr. 27, 1981

[51] Int. Cl.³ .................................. C07C 103/737
[52] U.S. Cl. ................................................ 564/123
[58] Field of Search ...................................... 564/123

[56] References Cited

U.S. PATENT DOCUMENTS

| | | | |
|---|---|---|---|
| 3,483,248 | 12/1969 | Pattison | 260/515 |
| 3,898,078 | 8/1975 | Fitzgerald et al. | 71/93 |
| 4,150,052 | 4/1979 | Watson et al. | 564/123 |
| 4,178,459 | 12/1979 | Watson et al. | 560/125 |
| 4,193,936 | 3/1980 | Watson et al. | 424/324 |
| 4,248,859 | 2/1981 | Rowsell et al. | 424/324 |

OTHER PUBLICATIONS

Wagner et al., Synthetic Organic Chemistry, John Wiley & Sons, N.Y., N.Y., 1955, p. 571.
Singleton et al., J.A.C.S. 60, (1938), pp. 540–543.

Primary Examiner—Arthur P. Demers
Attorney, Agent, or Firm—Arthur I. Palmer, Jr.; George E. Inskeep

[57] ABSTRACT

This invention provides an efficient two-step reaction sequence for producing N-t-butyl-p-menthane-3-carboxamide. The process involves forming 3-p-menthylmagnesium halide, and reacting the 3-p-menthylmagnesium halide with t-butyl isocyanate to form the product.

5 Claims, No Drawings

SYNTHESIS OF N-T-BUTYL-P-MENTHANE-3-CARBOXAMIDE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; and the like. The tobacco flavorants include compounds such as succinic anhydride; dihydroxyacetone; substituted pyridines; cinnamic derivatives; isovaleric acid; 6-methylhepta-3,5-dien-2-one; 2-butyl-2-butenal; 1,3-cyclohexadiene; alpha-pyrones; substituted butyrolacetones; pyrazines and thiazolidines; and the like.

Cooling compounds, particularly menthol, have been used extensively in tobacco products. Unfortunately, menthol has a high degree of volatility and also suffers from the disadvantage that it exhibits a relatively strong minty odor. Nevertheless, in spite of its disadvantages menthol is still extensively employed as a tobacco flavorant for the reason it has a physiological cooling effect on the mucous membranes of the mouth. Menthol flavorant in cigarette tobacco produces a cool sensation in the mouth during the smoking of a cigarette.

Other organic compounds are known which exhibit to some degree the properties of a physiological coolant. For example, N,N-dimethyl-2-ethylbutanamide is reported in French Pat. No. 1,572,332 as having a minty odor and a refreshing effect on mucous membranes. Other compounds of similar interest are 2,4,6-trimethylheptan-4-ol and 2,4,6-trimethylhept-2-en-4-ol as reported in Parfums-Cosmetiques-Savons, pages 17–20, May 1956.

More recently another group of organic compounds have been developed which are odorless and nonvolatile, and which can function as physiologically active coolants. These compounds are the subject matter of U.S. Pat. Nos. 4,178,459 and 4,193,936, and are generically classified as N-substituted para-menthane carboxamides. Illustrative of a particularly interesting species as a prospective smoking tobacco flavorant is N-t-butyl-p-menthane-3-carboxamide:

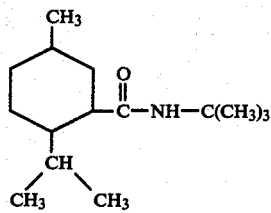

The said patents describe a sequence of conventional reactions for producing the N-substituted para-menthane carboxamides. Thus, N-t-butyl-p-menthane-3-carboxamide is produced by the following sequence of reactions:

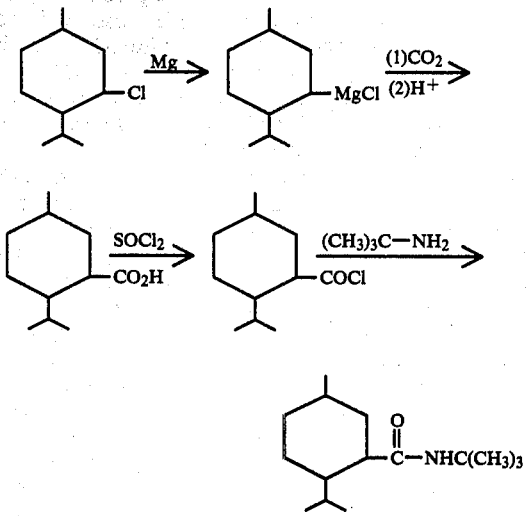

The reaction sequence is long and tedious, and the overall conversion from 3-p-menthyl halide to N-t-butyl-p-menthane-3-carboxamide is less than about 20 percent.

Accordingly, it is a main object of this invention to provide a novel process for producing N-(hydrocarbyl)substituted-p-menthane-3-carboxamide compounds.

It is a further object of this invention to provide a novel and efficient two-step reaction sequence for converting 3-p-menthyl halide to N-t-butyl-p-menthane-3-carboxamide.

Other objects and advantages of the present invention will become apparent from the accompanying description and examples.

DESCRIPTION OF THE INVENTION

One or more objects of the present invention are accomplished by the provision of a process for the synthesis of N-t-butyl-p-menthane-3-carboxamide which comprises (1) reacting 3-p-menthyl halide with magnesium in an anhydrous solvent medium to form 3-p-menthylmagnesium halide; and (2) reacting the 3-p-menthyl-magnesium halide with t-butyl isocyanate to form N-t-butyl-p-menthane-3-carboxamide product.

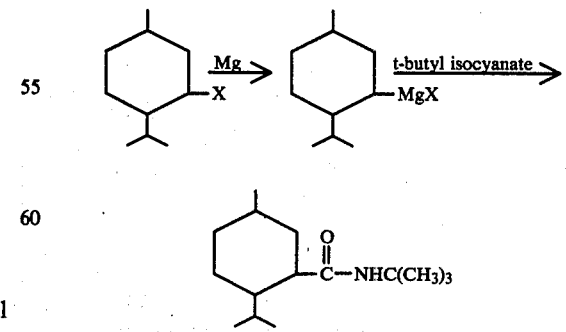

The 3p-menthyl halide reactant in step(1) preferably is selected from 3-p-menthyl chloride and 3-p-menthyl bromide.

The step(1) procedure is accomplished in accordance with conventional Grignard reagent preparation techniques. In a typical case, the step(1) reaction is conducted in a nonreactive solvent medium (e.g., diethyl ether) with the rigorous exclusion of moisture.

The step(1) reaction temperature will vary in the range between about 0° and 100° C., and normally will be in the range between about 20°–75° C.

The solvent solution of 3p-menthylmagnesium halide Grignard reagent obtained as a product of the step(1) procedure is in a convenient form for direct use in step(2) of the process. The quantity of Grignard reagent prepared in step(1) can be calculated to satisfy the prospective stoichiometry of the step(2) reaction.

The 3-p-menthylmagnesium halide and t-butyl isocyanate reactants in step(2) are employed in an approximately equimolar ratio, i.e., a halide:isocyanate ratio between about 0.8–1.2:1. The equimolar ratio facilitates product recovery and enhances the overall efficiency of the step(2) reaction.

The step(2) reaction is conducted at a temperature in the range between about −10° C. and 100° C., for a reaction period between about 1–20 hours. The reaction medium can be sampled and analyzed to monitor the progress of the step(2) reaction course toward completion.

An important aspect of the invention process is the high yield conversion which is achieved in the step(2) interaction of 3-p-menthylmagnesium halide with t-butyl isocyanate. Thus, unexpectedly it was found that the relative conversion efficiency of the reaction between 3-p-menthylmagnesium halide and t-butyl isocyanate is severalfold greater than the relative conversion efficiency of the reaction between 3-p-menthylmagnesium halide and carbon dioxide. It is to be noted that the latter carboxylation reaction is an intermediate step in the synthesis sequence illustrated above in connection with U.S. Pat. Nos. 4,178,459 and 4,193,936 in which the production of N-substituted para-menthane carboxamides is disclosed.

The following examples are further illustrative of the present invention. The reactants and other specific ingredients are presented as being typical, and various modifications can be derived in view of the foregoing disclosure within the scope of the invention.

EXAMPLE I

Preparation of N-t-Butyl-p-menthane-3-carboxamide

A.

Magnesium turnings (5.2 grams, 214 mg-atoms) were charged to a 3-necked flask, and anhydrous ether (10 milliliters) was added by means of a nitrogen-filled pipette. Crystals of iodine were added, and the mixture was stirred and heated at a temperature of 40° C. Simultaneously with the onset of heating, 3-menthyl chloride (10.0 grams, 57.2 mmoles) in 10 milliliters of anhydrous ether was added slowly. Heating and stirring were continued for an additional 1.75 hours after addition of 3-menthyl chloride was completed.

B.

The ethereal solution of 3-menthylmagnesium chloride Grignard reagent prepared in accordance with procedure A. was cooled to ice bath temperature, and t-butyl isocyanate (5.6 grams, 56.9 mmoles) in ether (10 milliliters) was added slowly. After the addition was completed, the reaction mixture was stirred overnight and then allowed to warm slowly. The reaction mixture was filtered through a stainless steel screen and a fritted glass funnel. The ethereal solution was washed successively with 5% hydrochloric acid, water, half-saturated sodium bicarbonate solution, and water, and then dried over magnesium sulfate. Removal of solvent yielded 10.18 grams (74.3%) of N-t-butyl-p-menthyl-3-carboxamide as a colorless solid.

EXAMPLE II

This Example illustrates a comparison of the relative efficiencies of the conversion of 3-menthyl chloride to p-menthane-3-carboxylic acid and to N-t-butyl-p-menthane-3-carboxamide.

3-Menthylmagnesium chloride was prepared in accordance with the procedure described in Example I, employing 30.0 grams (171.9 mmoles) of 3-methyl chloride in 5 milliliters of ether and 6.3 grams (257 mg-atoms) of magnesium turnings in 25 milliliters of ether. Two 25 milliliter ethereal aliquots of the reaction product solution were withdrawn in a protected moisture-free condition.

A.

Formation of p-Menthane-3-carboxylic acid

Dry carbon dioxide was introduced into one of the ethereal aliquots of 3-menthylmagnesium chloride Grignard reagent over a period of about 15 hours. After the addition of ether and water, the reaction mixture was acidified with 5% aqueous hydrochloric acid. The acidified mixture was filtered, and extracted with ether. The ethereal extract phase was contacted successively with portions of 10% aqueous sodium hydroxide solution.

The alkaline aqueous extract phase was washed with ether and then acidified with hydrochloric acid. The acidified solution was extracted with several portions of ether, and then the ethereal extract phase was dried over magnesium sulfate. Concentration of the solution under vacuum yielded 2.16 grams (11.7 mmoles) of p-menthane-3-carboxylic acid.

Formation of N-t-Butyl-p-menthane-3-carboxamide

The other ethereal aliquot of Grignard reagent prepared above was added to 7.8 grams (78.8 mmoles) of t-butyl isocyanate in 5 milliliters of ether with stirring, and then the reaction mixture was allowed to stand at room temperature for about 15 hours.

The solid cake which formed was subdivided and admixed with added ether. To the resultant slurry a 17 milliliter solution of 5% hydrochloric acid was added slowly.

After the evolution of gas had ceased, the phases were separated and the ether layer was washed successively with water, aqueous sodium bicarbonate solution, and water, and then dried over magnesium sulfate. After the removal of the solvent there was recovered a 13.55 grams (56.5 mmoles) yield of N-t-butyl-p-menthane-3-carboxamide.

C.

Comparison Of The A. And B. Reaction Efficiencies $$\frac{\text{mmole amide produced}}{\text{mmole acid produced}} = \text{relative efficiency}$$

$$\frac{56.6 \text{ mmole amide}}{11.7 \text{ mmole acid}} = 4.84$$

As the comparison data indicate, unexpectedly the reaction of 3-menthylmagnesium chloride with t-butyl isocyanate is almost five times more efficient than the reaction with carbon dioxide.

What is claimed is:

1. A process for the synthesis of N-t-butyl-p-menthane-3-carboxamide which comprises (1) reacting 3-p-menthyl halide with magnesium in an anhydrous solvent medium to form 3-p-menthylmagnesium halide; and (2) reacting the 3-p-menthylmagnesium halide with t-butyl isocyanate at a temperature between about $-10°$ C. and $100°$ C. to form N-t-butyl-p-menthane-3-carboxamide product.

2. A process in accordance with claim 1 wherein the 3-p-menthyl halide reactant in step(1) is 3-p-menthyl chloride.

3. A process in accordance with claim 1 wherein the 3-p-menthyl halide reactant in step(1) is 3-p-menthyl bromide.

4. A process in accordance with claim 1 wherein the 3-p-menthylmagnesium halide and t-butyl isocyanate reactants in step(2) are employed in about an equimolar ratio.

5. A process in accordance with claim 1 wherein the step(2) reaction is conducted over a period between about 1–20 hours.

* * * * *